(12) United States Patent
Cuschieri et al.

(10) Patent No.: US 6,925,668 B2
(45) Date of Patent: Aug. 9, 2005

(54) DEVICE FOR SUPPORTING AT LEAST ONE ARM OF AN OPERATING PERSON DURING A SURGICAL OPERATION

(75) Inventors: Alfred Cuschieri, St. Andrews Fife (GB); Timothy Graham Frank, Wormit Newport-On-Tay Fife (GB); Ian Rutherford, Dunee (GB); Donald McLean, Angus (GB); Stuart I. Brown, St. Andrews Fife (GB)

(73) Assignee: University of Dundee (GB)

( * ) Notice: Subject to any disclaimer, the term of this patent is extended or adjusted under 35 U.S.C. 154(b) by 0 days.

(21) Appl. No.: 10/866,969

(22) Filed: Jun. 14, 2004

(65) Prior Publication Data
US 2005/0015879 A1 Jan. 27, 2005

(30) Foreign Application Priority Data
Jun. 12, 2003 (EP) .......................................... 03013236

(51) Int. Cl.⁷ ............................................. A61G 7/075
(52) U.S. Cl. ............................................... 5/623; 5/621
(58) Field of Search .............................. 5/621–624, 646

(56) References Cited

U.S. PATENT DOCUMENTS

| 4,256,112 A | * | 3/1981 | Kopf et al. | ................. | 606/130 |
| 6,224,026 B1 | | 5/2001 | Dubois | ................... | 248/118.3 |
| 6,368,332 B1 | | 4/2002 | Salcudean et al. | .......... | 606/130 |
| 6,704,959 B2 | * | 3/2004 | Schuerch | ....................... | 5/648 |

FOREIGN PATENT DOCUMENTS

| DE | 28 32 500 | 7/1978 |
| DE | 41 09 388 | 4/1992 |
| DE | 195 04 838 | 7/1995 |
| EP | 0 868 885 | 10/1998 |

* cited by examiner

Primary Examiner—Heather Shackelford
Assistant Examiner—Fredrick Conley
(74) Attorney, Agent, or Firm—St. Onge Steward Johnston & Reens LLC

(57) ABSTRACT

A device for supporting at least one arm of an operating person during a surgical or medical operation comprises at least one supporting element for supporting the at least one arm of the operating person, the supporting element being arranged at a carrying structure for carrying the at least one supporting element. The carrying structure is configured such that the at least one supporting element can be lowered or raised for adjusting the height of the operating person's arm. The carrying structure comprises a control mechanism for lowering or raising the at least one supporting element, wherein the control mechanism includes a force load switch for activating the lowering or raising of the at least one supporting element, wherein the force load switch activates the lowering or raising of the at least one supporting element upon detecting compressive and/or tensile forces or motions acting via the at least one supporting element on the force load switch.

30 Claims, 3 Drawing Sheets

DEVICE FOR SUPPORTING AT LEAST ONE ARM OF AN OPERATING PERSON DURING A SURGICAL OPERATION

CROSS-REFERENCE TO OTHER APPLICATION

The present application claims priority of European patent application 03 013 263.9 filed on Jun. 12, 2003.

BACKGROUND OF THE INVENTION

The invention relates to a device for supporting at least one arm of an operating person during a surgical or medical operation.

A device of the kind mentioned at the outset, which can also be designated as an arm rest, is used as a support of the surgeon's or the surgical assistant's arm during an operation in order to increase steadiness of movement and reduce fatigue. Taking into consideration that a surgical operation can take up several hours and the surgical personnel carries out such an operation in a standing position, an arm rest of the aforementioned kind will be effective in avoiding a loss of preciseness of the manipulations carried out by the operating person.

The device comprises at least one supporting element for supporting the at least one arm of, for example, the surgeon. The supporting element is arranged at a carrying structure for carrying the at least one supporting element, wherein the carrying structure should be adapted to be mounted on a side of the operating table or in front of a surgical stool. However, the carrying structure of the device according to the invention can also be configured as a self-standing structure which can stand on the floor of the operating room beside the operating table.

A device known from DE 195 04 838 A1 is a supporting device integrated into an operating stool which can also be integrated in the operating table. The operating stool comprises an adjustable arm rest supporting the arms or hands of the surgeon leaning over the operating area.

However, in that document it is not disclosed how to adjust the height of the supporting element and, accordingly, the surgeon's or surgical assistance arm or hand.

SUMMARY OF THE INVENTION

Therefore, it is an object of the present invention to provide a device of the kind mentioned at the outset which allows the person the arm of which is supported by the at least one supporting element, to easily adjust the height of the at least one supporting element. The adjustment of the at least one supporting element should not distract the operating person from the surgical operation.

According to an aspect of the invention, a device for supporting at least one arm of an operating person during surgical or medical operation is provided, comprising a carrying structure carrying at least one supporting element for supporting the at least one arm of the operating person, the carrying structure being configured such that the at least one supporting element can be lowered or raised for adjusting the height of the operating person's arm, a control mechanism for lowering or raising the at least one supporting element, wherein the control mechanism includes a force load switch for activating the lowering or raising of the at least one supporting element, wherein the force load switch activates the lowering or raising of the at least one supporting element upon detecting at least one of compressive forces, tensile forces and motions acting via the at least one supporting element on the force load switch.

By means of the control mechanism including the force load switch for activating the lowering or raising of the at least one supporting element, the arm rest according to the present invention can be adjusted intuitively by the operating person, whose arm is supported by the device, by exerting compressive (push) and/or tensile (pull) forces on the at least one supporting element or by moving same. These compressive and/or tensile forces or motions can be simply exerted by the arm resting on the at least one supporting element even without moving the operating hand so that the surgeon or surgical assistant has not to interrupt the current manipulations within the surgical procedure in order to adjust the height of his or her arm. Thus, the device according to the invention renders it possible to intuitively adjust the height of his or her arm in order to find the most convenient position thereof. The adjustment of the at least one supporting element can be done very quickly and very easily without the need of specific tools or aid of other persons.

In a preferred refinement, the force load switch is designed such that the at least one supporting element remains in a tight position when the force load switch detects a force exerted by the at least one supporting element in an unloaded condition thereof or a compressive force exceeding the force in the unloaded condition.

While it would be possible within the scope of the invention to design the force load switch such that the supporting element is lowered or raised when a firm compressive force is exerted on the at least one supporting element, the present refinement has the advantage that the device is more reliable, because an unwanted lowering of the at least one supporting element is avoided when the user of the device heavily leans with his or her arm on the at least one supporting element. Also, in an unloaded condition of the at least one supporting element, i.e. when the force load switch detects substantially the weight of the at least one supporting element, the control mechanism is inactivated and the at least one supporting element maintains its position.

In a further preferred refinement, the control mechanism is designed such that the at least one supporting element is lowered or raised when the force load switch detects tensile forces.

Again, this measure has the advantage that the control mechanism for lowering or raising the at least one supporting element is only activated when the operating person raises his or her arm at least slightly. In the normal operating position of the operating person with his or her arm resting on the at least one supporting element the control mechanism is inactivated thereby avoiding lowering or raising of the at least one supporting element when it is not desired by the operating person.

In a further preferred refinement the control mechanism is designed such that the at least one supporting element remains in its height position when the force load switch detects a tensile force which is in a range of about 0 to about 5 N, preferably about 0 to about 2 N.

This measure has the advantage that the control mechanism is not too sensitive to the movement of the arm of the user when carrying out the necessary manipulations within, for example, the surgical procedure. This means that even in case that the user raises his or her arm slightly, the control mechanism is not activated and the supporting element remains in its position.

In this connection, it is further preferred if the maximum tensile force which does not activate the control mechanism, is adjustable.

In that way, the sensitivity of the device can be adapted to the specific requirements of the respective person using the device.

In a further preferred refinement, the control mechanism is designed such that the at least one supporting element is lowered, when the force load switch detects a tensile force exceeding a first upper force limit at which the at least one supporting element still remains in its position, and the supporting element is raised, when the force exceeds a second upper force limit at which the supporting element is lowered.

Thus, the at least one supporting element can be lowered by the surgeon or surgical assistant the arm of which rests on the at least one supporting element by raising his or her arm by a small force, wherein it is not necessary to move the hand or hands which can continue to carry out the manipulations in the surgical operation. Lowering of the at least one supporting element is, thus, highly facilitated by just raising the arm supported by the at least one supporting element. The lowering of the at least one supporting element is then stopped by just leaning again the arm on the at least one supporting element, as described before.

Furthermore, raising of the supporting element can also easily be activated by the surgeon or surgical assistant him- or her-self by exerting a larger tensile force on the at least one supporting element. Again, the raising of the at least one supporting element is stopped by just resting the arm on the at least one supporting element.

In a further preferred refinement the control mechanism is designed such that the supporting element is raised only, when the force detected by the force load switch exceeds the second upper force limit by a predetermined amount.

The advantage here is that the forces for lowering the supporting element on the one hand and raising the supporting element on the other hand are sufficiently distinguishable for the user of the device. Thus, an unwanted switching between the lowering of the at least one supporting element and the raising of the at least one supporting element is avoided.

In a further preferred refinement the control mechanism is designed such that the at least one supporting element is lowered when the force load switch detects a tensile force which is a range of about 0 to 10 N, preferably about 2 to about 6 N.

In a further preferred refinement the control mechanism is designed such that the at least one supporting element is raised when the force load switch detects a tensile force which is at least about 3 N, preferably at least about 8 N.

In a further preferred refinement, the control mechanism is designed such that the at least one supporting element is raised only when the force load switch detects a tensile force which is at least about 1 N, preferably about 2 N larger than the maximum force responsive to which the force load switch activates lowering of the at least one supporting element.

The aforementioned ranges and values of forces upon detection of which the force load switch activates the lowering, the raising or inactivates same, can easily be summoned up without large efforts by the user and represent advantageous examples of the first and second upper force limits mentioned before.

It is to be understood that the above references to "tensile" forces can also be understood as forces which lower the weight exerted on the force load switch by the at least one supporting element in the unloaded condition thereof. The latter force can be regarded as the zero point of the force, while compressive forces have a negative value and tensile forces a positive value.

While in the afore-going the activating of the lowering or raising of the at least one supporting element has been described by raising the surgeon's or surgical assistance arm by tensile forces in different degrees, it can be also envisaged within the scope of the present invention to activate lowering and raising of the at least one supporting element by exerting the tensile forces in different directions, for example, by exerting a force onto the at least one supporting element in opposite sideward directions.

In a further preferred refinement the carrying structure comprises at least one carrying arm, which is pivotable about a horizontal or substantially horizontal pivot axis in substantially upward and/or downward direction such that pivoting of the carrying arm about the pivot axis raises or lowers the at least one supporting element.

This measure has the advantage that changes of the height position of the at least one supporting element can be adjusted in a suitable manner by changing the angle of the at least one carrying arm carrying the at least one supporting element.

In this connection it is preferred if the at least one carrying arm is pivotable about the horizontal or substantially horizontal axis in a range of about +50° to −50°, preferably +20° to −25°, with respect to the horizontal.

With this range of angles of movement of the at least one carrying arm a sufficient large range of continuous height positions of the at least one supporting element can be adjusted. By limiting the movement of the at least one carrying arm in downward direction it is advantageously prevented that the at least one carrying arm comes into contact with the patient, also in a fault condition of the device.

In a further preferred refinement the at least one carrying arm is pivotable about a vertical or substantially vertical pivot axis, the arm being preferably pivotable by 360° about this axis.

This measure has the advantage that not merely the height position of the at least one supporting element can be adjusted, but the at least one supporting element can also be moved in other spatial directions so that the surgeon's or surgical assistant's arm can be moved in positions most convenient for the specific manipulation to be carried out in the surgical operation, while permanently supported by the at least one supporting element.

If the afore-mentioned pivot axis is inclined with respect to the vertical and oriented in a proper direction, the supporting element can move on a curved path with respect to the horizontal when pivoted about the axis, and is in its lowest position near to the surgical site.

In a further preferred refinement the control mechanism further comprises a stop cooperating with the at least one carrying arm for controlling the pivotement of the carrying arm, the stop being arranged under the carrying arm for supporting same and being movable in vertical or substantially vertical direction.

At least in case that the carrying arm is also pivotable about a vertical or substantially vertical axis, the stop is arranged such that it moves with the carrying arm.

By means of the stop a constructional simple mechanism for lowering and raising the at least one carrying arm and, thereby, the at least one supporting element is provided. The further advantage is that the stop, arranged under the carrying arm, prevents dropping of the carrying arm onto the patient in a fault condition of the device.

In this context, it is preferred if the stop is driven by an electrical motor which is activated by the force load switch.

By this measure, the control mechanism can be constituted by a low number of parts, namely the force load switch, the adjustable stop and the electrical motor resulting in a low cost arm rest device.

In a further preferred refinement the power of the motor is small such that it is not sufficient to overcome the frictional forces of the carrying structure to lower the stop, except a tensile force is exerted on the at least one supporting element.

This measure has the advantage that the motor can never lower the at least one supporting element in a fault condition, for example in case that the force load switch triggers the motor to lower the stop although the at least one supporting element is in an unloaded condition or even in a loaded condition.

In a further preferred refinement a signalling device is provided generating an audible and/or visible signal when the at least one supporting element is being lowered or raised.

The advantage of this measure is that the user of the device can immediately recognize a movement of the at least one supporting element in upward or downward direction. Thus, when the user of the device wishes to lower or raise the at least one supporting element and activates the lowering or raising by, for example, exerting respective tensile forces onto the at least one force load switch as described before, he or she can immediately verify by the audible or visible signal as to whether his or her command has triggered the desired motion of the at least one supporting element.

In this context, it is preferred if the signalling device generates different signals for upward and downward motion of the at least one supporting element.

By this measure, the feedback of the movement of the control mechanism to the user is improved, because it is rendered possible to distinguish between the upward and downward motion due to the different signals for both motions.

In a further preferred refinement the at least one supporting element has a portion for supporting the arm and at least one portion for the arm to exert tensile forces on the supporting element.

This measure has the advantage that, on the one hand, the surgeon's or surgical assistant's arm can rest securely on the at least one supporting element, and, on the other hand, this configuration of the at least one supporting element allows the user of the device to command the lowering and raising of the at least one supporting element as described above, namely by simply exerting tensile forces onto the force load switch via the at least one supporting element without the need of using the hand of the other arm, and without moving the hand of the arm supported by the at least one supporting element.

In a further preferred refinement the at least one supporting element has a lateral opening for withdrawing the arm from the supporting element.

This measure has the advantage that the surgeon has to simply slide the arm out sideways from the at least one supporting element for removing his arm from the device.

In a further preferred refinement the at least one supporting element is attached at the carrying structure in a manner pivotable about a horizontal or substantially horizontal pivot axis and/or about a vertical or substantially vertical pivot axis.

By this measure, the number of the degrees of freedom of movement of the at least one supporting element is further enhanced so that the user can move his or her arm in the most convenient position with respect to the operating side, while the arm is permanently supported from underneath.

In this context, it is preferred if the at least one supporting element is pivotable about the horizontal axis by an angle in a range of +90° to −90° with respect to the vertical and/or about the vertical axis by 360°.

With these ranges of possible motions of the at least one supporting element, an optimal adjustability of the at least one supporting element is provided.

In a further preferred refinement the carrying structure comprises a mounting portion adapted for attaching the structure at the side rail of an operating table.

In this configuration, the device according to the invention can be advantageously attached at a side of an operating table. The device can thus support the user's arm or arms from the same or the opposite side of the operating table. The mounting portion can comprise a clamp, and the mounting portion can be configured such that the device can be quickly removed from the operating table by lifting it out of the clamp.

In a further preferred refinement the device comprises two supporting elements for independently supporting both arms of a surgeon during a surgical operation.

By this measure, the advantage is achieved that both arms of a surgeon or surgical assistant can be supported during a surgical operation, thereby further reducing fatigue and enhancing the precision of the manipulations carried out by the operating person.

Further features and advantages will be apparent from the following description and the accompanying drawings.

It is to be understood that the features mentioned before and those features yet to be explained hereinafter are not only applicable in the given combination, but also in other combinations or in isolation without departing the scope of the present invention.

BRIEF DESCRIPTION OF THE DRAWINGS

An exemplary embodiment of the invention is depicted in the drawings and will be explained below with reference to the drawings. In the drawings.

DETAILED DESCRIPTION OF A PREFERRED EMBODIMENT

Figure 1:
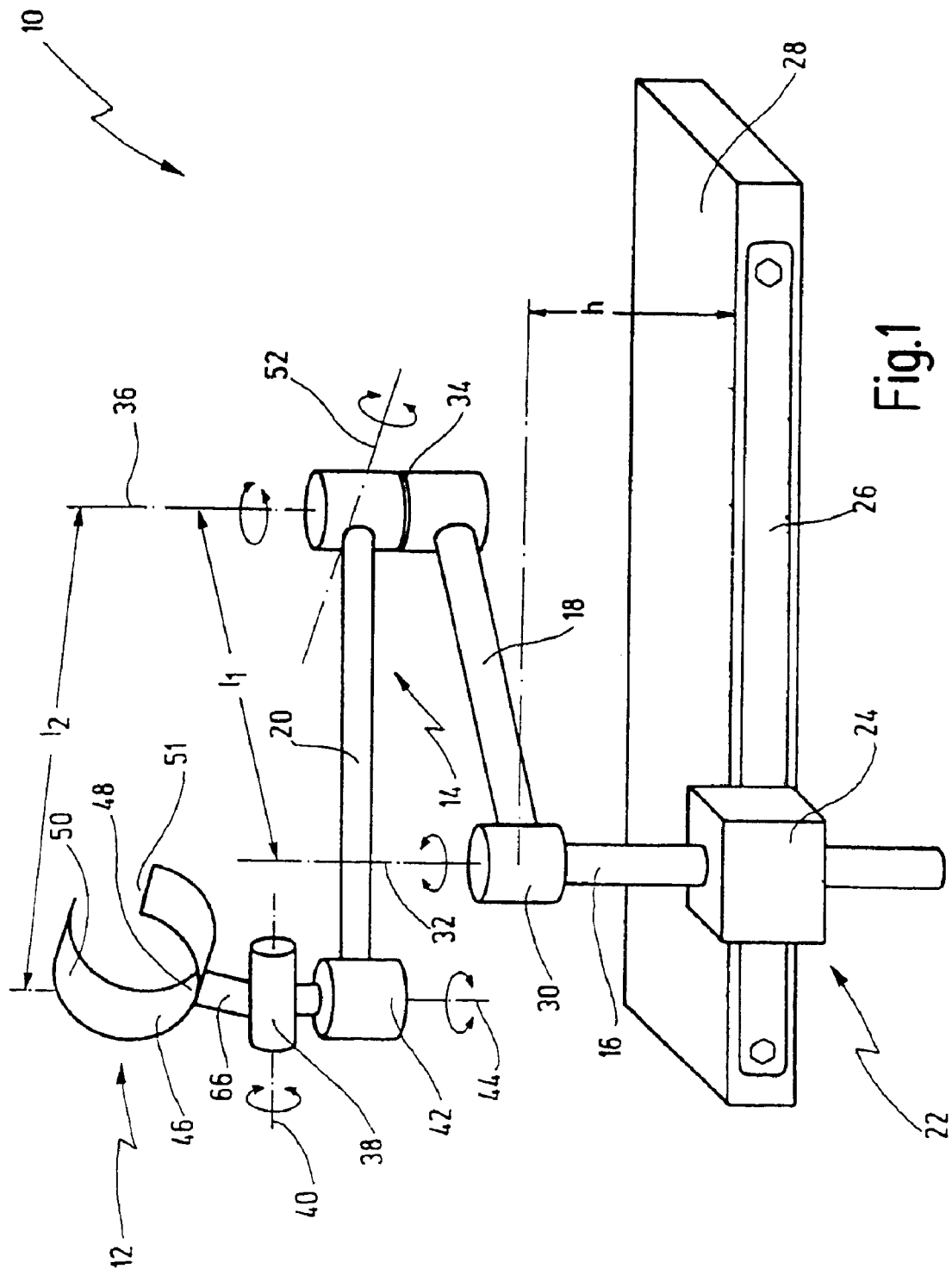
FIG. 1 shows a device for supporting at least one arm of an operating person during a surgical or medical operation in its entirety and mounted on an operating table.

FIG. 1 shows a device labelled in its entirety with reference numeral 10 for supporting at least one arm of an operating person (not shown) during a surgical or medical operation.

The device 10 can be used for all surgical disciplines.

The device 10 comprises at least one supporting element 12 for supporting the at least one arm of, for example, the surgeon or surgical assistant.

The supporting element 12 is arranged at a carrying structure 14 for carrying the at least one supporting element 12.

The carrying structure 14 comprises a first carrying arm extending vertically or substantially vertically, a second carrying arm 18 extending horizontally or substantially horizontally, and a third carrying arm 20 extending horizontally or substantially horizontally.

The carrying structure 14 further comprises a mounting portion 22 comprising a clamp 24 receiving the first carrying arm 16. The clamp 24 can be attached to a rail 26 of an operating table 28. The first carrying arm 16 can be lifted out of the clamp 24 for removing the device 10 from the table 28.

A height h of the second carrying arm 18 can be adjusted by vertically moving the first carrying arm 16 within the clamp 24. The height h of the second carrying arm 18 from the top of the rail 26 can be adjusted in a range from 100 to 600 mm, preferably from 120 to 570 mm.

The first carrying arm 16 is connected with the second carrying arm 18 via a first joint 30. The second carrying arm 18 can be pivoted about a first vertical or substantially vertical axis 32 by an angle of from 0° to 360°. A length $l_1$ of the second carrying arm 18 is in the range of 120 mm to 250 mm, and is preferably about 180 mm.

The third carrying arm 20 is connected with the second carrying arm 18 by a second joint 34. The second joint 34 allows the third carrying arm 20 to pivot about a second vertical or substantially vertical pivot axis 36 in a range of 0° to 360°, preferably. A length $l_2$ of the third carrying arm 20 is in the range of about 150 mm to 350 mm, preferably 250 mm.

The supporting element 12 is arranged at the outermost end of the third carrying arm 20 and extends substantially upright from the latter. Further, the supporting element 12 is mounted on a third joint 38 allowing the supporting element 12 to pivot about a first horizontal or substantially horizontal axis 40 in a range from about −90° to +90° with respect to the vertical. In addition, the supporting element 12 is connected with the third carrying arm 20 via a fourth joint 42 allowing the supporting element 12 to be pivoted about a third vertical or substantially vertical pivot axis 44 in a range from 0° to 360°.

The supporting element 12 is configured in form of a cup such that it surrounds the arm of the operating person when inserted into the cup by at least 180°, preferably 270° as shown in FIG. 1. In other words, the supporting element 12 has at least one lower portion 48 on which the arm, in most cases the forearm of the operating person can rest, and an upper portion 50 which is arranged above or on the upper side of the arm of the operating person when inserted in the cup. In addition the supporting element 12 has a lateral opening 51 for withdrawing the surgeon's arm.

Further, the carrying structure 14 is configured such that the at least one supporting element 12 can be lowered or raised for preferably continuously adjusting the height of the arm of the operating person as will be described hereinafter in more detail. It is to be understood that the aforementioned adjustment of the height of the supporting element 12 is provided in addition to the height adjustability of the first carrying arm 16 which has been already described above.

The adjustment of the supporting element 12 to be described hereinafter is, rather than the adjustability of the first carrying arm 16, a self-adapting adjustability, which is actuated by a control mechanism which will be described below.

The carrying structure 14 is configured such that at least the third carrying arm 20 is also pivotable about a second horizontal or substantially horizontal pivot axis 52. The range of pivotment of the third carrying arm 20 about the axis 52 is from about +30° to −30° from the horizontal, preferably from about +20° to about −25°.

Figure 2:
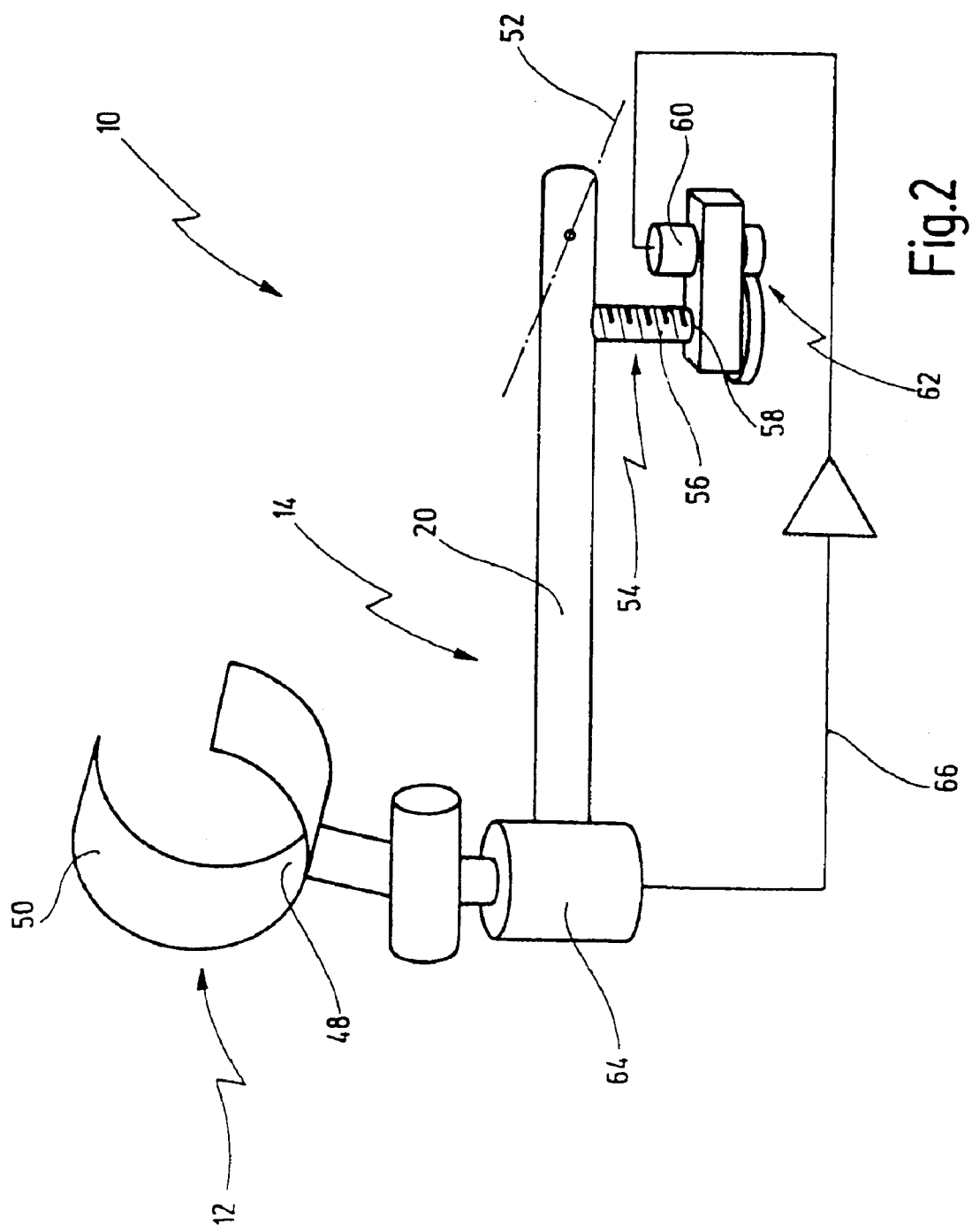
FIG. 2 the device of claim 1 in part in an enlarged scale showing details of the control mechanism for lowering and raising the at least one supporting element of the device.

With reference to FIG. 2, the control mechanism comprises a stop 54 arranged under the third carrying arm 20 in a distance from the pivot axis 52 and movable together with the third carrying arm 20 when the latter is pivoted about the axis 36. The stop 54 cooperates with the third carrying arm 20 by supporting same from the underside thereof. The stop 54 is configured as a threaded rod 56 which passes through a stationary threaded bore 58. By rotating the threaded rod 56 about its longitudinal axis in the one or the other direction, the stop 54 moves upward or downward in vertical direction and, thereby, raises or lowers the third carrying arm 20 and, thus, the supporting element 12.

The stop 54 is immovable with respect to the third carrying arm except the upward and downward motion for pivoting the carrying arm 20 as described before.

The stop 54 is driven by an electrical motor 60. The electrical motor 60 is bi-directional in order to rotate the stop 54 in the one or the other direction, and is operatively connected with the stop 54 via a gear arrangement 62, for example.

The control mechanism further includes a force load switch 64, which is configured as a load cell, which is operatively connected with the supporting element 12 and activates the lowering or raising of the supporting element 12 upon detecting compressive and/or tensile forces acting via the supporting element 12 on the force load switch 64.

The force load switch 64 is connected with the electrical motor 60 via a control circuit, which is simply illustrated in FIG. 2 as a line 66.

In dependence on tensile and/or compressive forces, the force load switch 64 activates the motor 60 to rotate the stop 54 in the one direction for raising the supporting element 12, or in the opposite direction for lowering the supporting element 12, or the force load switch 64 stops the electrical motor 60 so that the supporting element 12 remains in the adjusted position, as will be described hereinafter in more detail with reference to FIG. 3.

Figure 3:
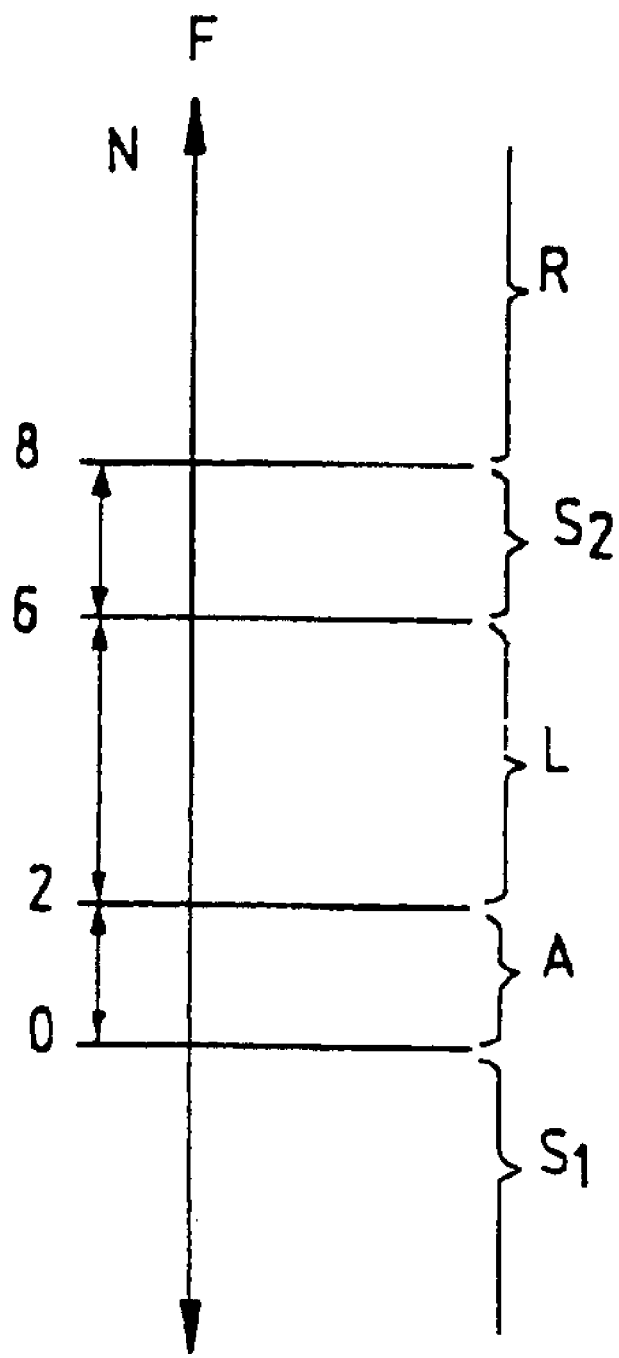
FIG. 3 a force load diagram explaining the triggering of the lowering and raising the supporting element of the device in FIGS. 1 and 2.

FIG. 3 shows a diagram where the force F acting on the force load switch 64 is drawn as a vector, and, therefore can have positive values and negative values. The zero point (0 N) has been chosen in this representation as the force which is detected by the force load switch 64 in an unloaded condition of the supporting element 12. This is the condition when the supporting element 12 acts with its own weight together with the structural parts of the carrying structure 14 between the force load switch 64 and the supporting element 12 on the force load switch 64. In this condition, i.e. when the force load switch 64 detects a force of 0 N, the force load switch 64 does not activate the motor 60 or gives a signal to the electrical motor 60 to stand still.

The supporting element 12 also remains in its height position when the force load switch 64 detects a compressive force exceeding the force in the unloaded condition of the supporting element 12. This is the case when the surgeon has inserted his or her arm into the supporting element 12 and leans on the lower portion 48 thereof. Such compressive forces correspond to a negative value of the force F. In each case, when the force F has a negative value the supporting element 12 remains in its height position. Nevertheless, the supporting element 12 can be moved about the horizontal axis 40 and about the vertical axis 44 in this situation, and also the movements of the carrying arms 20 and 18 about the axis 36 and 32 are free in this situation while the surgeon's arm securely rests on the supporting element 12.

A connecting arm 66 between the supporting element 12 and the joint 38 is as short as possible in order to not diminish the sensation of the surgeon's arm and not to affect the preciseness of the surgical operation.

There is another interval A of forces F from about 0 to about 5 N, in the present embodiment from about 0 to about 2 N of tensile forces which will also not cause the force load switch 64, when detected by it to activate the motor 60 to lower or to raise the stop 54. Thus, range A is a buffer range of forces, the upper limit of which is preferably adjustable to the requirements of the user of the device 10 and which prevents undesired activating of the motor 60 for lowering or raising the supporting element 12. In other words, interval A prevents the device 10 being too sensitive to the movements of the surgeon's arm which normally occur in a surgical procedure, for example when operating a medical instrument.

Following to range A there is a range L of tensile forces which, when detected by the force load switch 64 cause the latter to activate the motor 60, namely to rotate the stop 54 in a direction which lowers the stop 54 and, therefore, the third carrying arm 20 and, thereby, the supporting element 12.

In the present embodiment, the range L begins at about 2 N and ends at about 6 N, but the lower limit of the range L can also be 0 N and 10 N; the upper limit can be about the limits can preferably be adjustable according to the surgeon's needs.

Another range R of tensile forces F which exceed at least about 3 N, in the present embodiment at least about 8 N cause the force load switch 64 when detected by same to trigger the electrical motor 60 to rotate the stop 64 in the opposite direction in order to raise the stop 54, thus the third carrying arm 20 and, thereby, the supporting element 12.

The tensile forces mentioned before can simply be exerted by the surgeon's arm inserted in the supporting element 12 by raising the surgeon's arm in the supporting element 12 and thereby coming into contact with the upper portion 50 of the supporting element 12, thereby exerting the activation force onto the force load switch 64. Thus, in order to lower the supporting element 12, the surgeon raises his or her arm with a small force, and in order to raise the supporting element 12, he or she raises the arm with a larger force. In any case, the surgeon can keep the hand of the same arm supported by the supporting element still so that there is no interference between adjusting the height position of the supporting element and the surgical procedure actually carried out.

In order to increase the operational safety of the device, there is provided another range $S_2$ of forces, namely tensile forces which, when detected by the force load switch 64, do not cause same to activate the electrical motor 60, but to stop the motor 60 or to inactivate the motor 60 thereby maintaining the actual height position of the supporting element 12. This range $S_2$ of forces is an interval of at least 1 N, preferably at least about 2 N above the maximum force responsive to which the force load switch 64 would activate lowering of the supporting element 12, i.e. preferably about 2 N larger than the upper limit of the range L of forces.

The power of the electrical motor 60 is chosen such that friction in the device 10 can only be overcome when the operating person takes some of the weight of the carrying structure 14 by raising his or her arm in the supporting element 12.

Further, the power of the motor is preferably such that the supporting element 12 goes from fully lowered to fully raised in approximately ten seconds.

The device 10 further comprises a signalling device (not shown) for generating an audible and/or visible signal when the at least one supporting element 12 is being lowered or raised. The signalling device generates different signals for upward and downward motion of the at least one supporting element 12.

What is claimed is:

1. A device for supporting at least one arm of an operating person during a surgical or medical operation, comprising:
   a carrying structure carrying at least one supporting element for supporting said at least one arm of said operating person, said carrying structure being configured such that said at least one supporting element can be lowered or raised for adjusting the height of said operating person's arm,
   a control mechanism for lowering or raising said at least one supporting element, wherein said control mechanism includes a force load switch for activating said lowering or raising of said at least one supporting element, wherein said force load switch activates said lowering or raising of said at least one supporting element upon detecting at least one of compressive forces, tensile forces and motions acting via said at least one supporting element on said force load switch.

2. The device of claim 1, wherein said control mechanism is designed such that said at least one supporting element remains in its height position when said force load switch detects a force exerted by said at least one supporting element in an unloaded condition of said supporting element or a compressive force exceeding said force in said unloaded condition.

3. The device of claim 1, wherein said control mechanism is designed such that said at least one supporting element is lowered or raised when said force load switch detects tensile forces.

4. The device of claim 1, wherein said control mechanism is designed such that said at least one supporting element remains in its height position when said force load switch detects a tensile force which is in a range of about 0 to about 5 N.

5. The device of claim 1, wherein said control mechanism is designed such that said at least one supporting element remains in its height position when said force load switch detects a tensile force which is in a range of about 0 to about 2 N.

6. The device of claim 1, wherein a maximum tensile force which does not activate said lowering or raising, is adjustable.

7. The device of claim 1, wherein said control mechanism is designed such that said at least one supporting element is lowered, when said force load switch detects a tensile force exceeding a first upper force limit at which said at least one supporting element still remains in its position, and said supporting element is raised, when said force exceeds a second upper force limit at which said supporting element is lowered.

8. The device of claim 7, wherein said control mechanism is designed such that said supporting element is raised only, when said force detected by said force load switch exceeds said second upper force limit by a predetermined amount.

9. The device of claim 1, wherein said control mechanism is designed such that said at least one supporting element is lowered when said force load switch detects a tensile force which is in a range of about 0 to about 10 N.

10. The device of claim 1, wherein said control mechanism is designed such that said at least one supporting element is lowered when said force load switch detects a tensile force which is in a range of about 0 to about 6 N.

11. The device of claim 1, wherein said control mechanism is designed such that said at least one supporting element is raised when said force load switch detects a tensile force which is at least about 3 N.

12. The device of claim 1, wherein said control mechanism is designed such that said at least one supporting element is raised when said force load switch detects a tensile force which is at least about 8 N.

13. The device of claim 1, wherein said control mechanism is designed such that said at least one supporting element is raised only when said force load switch detects a tensile force which is at least about 1 N larger than a maximum force responsive to which said force load switch activates said lowering of said at least one supporting element.

14. The device of claim 1, wherein said carrying structure comprises at least one carrying arm, which is pivotable about a substantially horizontal pivot axis in substantially vertical direction such that pivoting of said carrying arm about said pivot axis raises or lowers said at least one supporting element.

15. The device of claim 14, wherein said at least one carrying arm is pivotable about said substantially horizontal axis in a range of about +50° to −50° with respect to a horizontal line.

16. The device of claim 11, wherein said at least one carrying arm is pivotable about a substantially vertical pivot axis.

17. The device of claim 16, wherein said at least one carrying arm is pivotable about said substantially vertical pivot axis by approximately 360°.

18. The device of claim 1, wherein said carrying structure comprises at least one carrying arm, and wherein said control mechanism further comprises a stop cooperating with said at least one carrying arm for controlling a pivotment of said carrying arm, said stop being arranged under said carrying arm for supporting same and being movable in substantially vertical direction.

19. The device of claim 18, wherein said stop is driven by an electrical motor which is activated by said force load switch.

20. The device of claim 19, wherein a power of said motor is small such that it is not sufficient to overcome frictional forces of said carrying structure to lower said stop, except a tensile force is exerted on said at least one supporting element.

21. The device of claim 1, wherein a signalling device is provided generating a signal when said at least one supporting element is being lowered or raised.

22. The device of claim 21, wherein said signalling device generates different signals for upward and downward motion of said at least one supporting element.

23. The device of claim 1, wherein said at least one supporting element has a portion for supporting said arm of said operating person and at least one portion for said arm to exert tensile forces on said supporting element.

24. The device of claim 1, wherein said at least one supporting element has a lateral opening for withdrawing said operating person's arm from said supporting element.

25. The device of claim 1, wherein said at least one supporting element is attached at said carrying structure in a manner pivotable about a substantially horizontal pivot axis.

26. The device of claim 1, wherein said at least one supporting element is attached at said carrying structure in a manner pivotable about a substantially vertical pivot axis.

27. The device of claim 25, wherein said at least one supporting element is pivotable about said substantially horizontal axis by an angle in a range of +90° to −90°.

28. The device of claim 26, wherein said at least one supporting element is pivotable about said substantially vertical axis by about 360°.

29. The device of claim 1, wherein said carrying structure comprises a mounting portion adapted for attaching said carrying structure at a side rail of an operating table.

30. The device of claim 1, wherein said device comprises two supporting elements for independently supporting both arms of said operating person during a surgical or medical operation.

* * * * *